(12) United States Patent
Cornell et al.

(10) Patent No.: US 12,605,417 B2
(45) Date of Patent: **\*Apr. 21, 2026**

(54) COMPOSITIONS AND METHODS FOR AMELIORATING SYMPTOMS ASSOCIATED WITH INFLAMMATORY SKIN DISORDERS

(71) Applicant: CODEX LABS CORPORATION, San Jose, CA (US)

(72) Inventors: Marc Cornell, San Jose, CA (US); Barbara A. Paldus, San Jose, CA (US); Mark Selker, San Jose, CA (US); Paula Simpson-Nilsen, Whitby (CA)

(73) Assignee: CODEX LABS CORPORATION, San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/900,196

(22) Filed: Sep. 27, 2024

(65) Prior Publication Data

US 2026/0091071 A1      Apr. 2, 2026

(51) Int. Cl.
*A61K 36/00* (2006.01)
*A61K 31/164* (2006.01)
(Continued)

(52) U.S. Cl.
CPC ............ *A61K 36/03* (2013.01); *A61K 31/164* (2013.01); *A61K 31/4172* (2013.01); *A61K 31/728* (2013.01); *A61K 35/745* (2013.01); *A61K 35/747* (2013.01); *A61K 36/28* (2013.01); *A61K 36/30* (2013.01); *A61K 36/53*

(2013.01); *A61K 36/577* (2024.05); *A61K 36/61* (2013.01); *A61K 36/80* (2013.01); *A61K 36/899* (2013.01); *A61P 17/00* (2018.01)

(58) Field of Classification Search
None
See application file for complete search history.

(56) References Cited

U.S. PATENT DOCUMENTS 10,682,306 B1    6/2020    Ryan et al.
10,721,937 B1    7/2020    Cornell et al.
(Continued)

FOREIGN PATENT DOCUMENTS

BG          3819 U1 *    7/2020
JP      5465037 B2        4/2014
(Continued)

OTHER PUBLICATIONS

WO2018178712A1, machine translation, 26 pages (Year: 2018).*
(Continued)

*Primary Examiner* — Amjad Abraham
(74) *Attorney, Agent, or Firm* — MEDLER FERRO WOODHOUSE & MILLS PLLC

(57) ABSTRACT

The present invention is directed to compositions and methods for ameliorating symptoms associated with inflammatory skin disorders involving applying a synergistic blend of plant-based actives containing: (1) a synergistic blend of at least: (a) *Calendula officinalis* stem cell extract; (b) *Symphytum officinale* extract; (c) a biotech-derived *Haberlea rhodopensis* extract; and (d) *Padina pavonica thallus* extract; and (2) at least one skin protectant active ingredient.

29 Claims, 1 Drawing Sheet

(51) Int. Cl.

| | |
|---|---|
| *A61K 31/4172* | (2006.01) |
| *A61K 31/728* | (2006.01) |
| *A61K 35/745* | (2015.01) |
| *A61K 35/747* | (2015.01) |
| *A61K 36/03* | (2006.01) |
| *A61K 36/185* | (2006.01) |
| *A61K 36/28* | (2006.01) |
| *A61K 36/30* | (2006.01) |
| *A61K 36/53* | (2006.01) |
| *A61K 36/61* | (2006.01) |
| *A61K 36/80* | (2006.01) |
| *A61K 36/899* | (2006.01) |
| *A61P 17/00* | (2006.01) |

(56) References Cited

U.S. PATENT DOCUMENTS

| | | | |
|---|---|---|---|
| 2002/0151584 A1 | 10/2002 | Huang et al. | |
| 2007/0048243 A1* | 3/2007 | Hansenne | A61K 36/03 |
| | | | 424/195.17 |
| 2008/0014162 A1* | 1/2008 | Willemin | A61K 8/602 |
| | | | 424/773 |
| 2010/0233110 A1 | 9/2010 | Cohen et al. | |
| 2014/0349375 A1 | 11/2014 | Benjamin et al. | |
| 2015/0118334 A1* | 4/2015 | Rozenblat | A61K 36/539 |
| | | | 424/745 |
| 2016/0256368 A1 | 9/2016 | Santhanam et al. | |
| 2019/0111093 A1 | 4/2019 | Siurkus et al. | |
| 2020/0002377 A1 | 1/2020 | Van Den Nest et al. | |
| 2022/0110845 A1* | 4/2022 | Plows | A61K 9/0014 |
| 2022/0378690 A1* | 12/2022 | Ryan | A61K 36/28 |
| 2023/0248798 A1* | 8/2023 | Webb | A61K 47/14 |
| | | | 424/750 |
| 2024/0115643 A1* | 4/2024 | Franklin | A61K 31/704 |
| 2024/0358787 A1* | 10/2024 | Chen | A61P 17/02 |

FOREIGN PATENT DOCUMENTS

| | | | | |
|---|---|---|---|---|
| WO | 2012/033422 A1 | 3/2012 | | |
| WO | WO-2018178712 A1 * | 10/2018 | | A61K 33/38 |
| WO | 2023/205439 A2 | 10/2023 | | |
| WO | WO-2024098120 A1 * | 5/2024 | | A61K 36/185 |

OTHER PUBLICATIONS

BG-3819-U1, machine translation, 8 pages (Year: 2020).*
Staneva et al. Haberlea rhodopensis Extract Tunes the Cellular Response to Stress by Modulating DNA Damage, Redox Components, and Gene Expression, Int. J. Mol. Sci. 2023, 24, 15964. https://doi.org/10.3390/ijms242115964 (Year: 2023).*
Website (Feb. 14, 2024) incidecoder.com, Dr. Schrammek Special Care Cream (Year: 2024).*
Bang et al., "Integrated bioinformatic analysis of gene expression profiling data to identify combinatorial biomarkers in inflammatory skin disease," Sci. Report 12: 5889 (2022).
Blunder et al., "PPARdelta in affected atopic dermatitis and psoriasis: a possible role in metabolic programming," Int. J. Mol. Sci. 22(14): 7354 (2021).
Boudjadi et al., "The expression and function of PAX3 in development and disease," Gene 666: 145-157 (2018).
Budu-Aggrey et al., "European and multi-ancestry genome-wide association meta-analysis of atopic dermatitis highlights importance of systemic immune regulation," Nature Comm. 14: 6172 (2023).
Chen et al., "Effects of different extraction techniques on physicochemical properties and activities of polysaccharides from comfrey (*Symphytum officinale* L.) root," Industrial Crops & Prods. 121: 18-25 (2018).
Chiricozzi et al., "Targeting IL-4 for the Treatment of Atopic Dermatitis," Immunotargets Ther. 9:151-156 (2020).

Coleman et al., "Rho GTPase signaling pathways in the morphological changes associated with apoptosis," Cell Death Differ. 9: 493-504 (2002).
Costanzo et al., "The Biology and Function of Tissue Inhibitor of Metalloproteinase 2 in the Lungs," Pulm. Med. 2022: 3632764 (2022).
Edamitsu et al., "AHR and NRF2 in Skin Homeostasis and Atopic Dermatitis," Antioxidants 11(2): 227 (2022).
Elysium Health, "What Is Your Skin Barrier, And Why Should You Protect It?" p. 1-13. Retrieved from the Internet: URL: https://www.elysiumhealth.com/blogs/aging101/what-is-the-skin-barrier.
Facheris et al., "The translational revolution in atopic dermatitis: the paradigm shift from pathogenesis to treatment," Cell Mol. Immunol. 20: 448-474 (2023).
Fania et al., "Multiple roles for cytokines in atopic dermatitis: from pathogenic mediators to endotype-specific biomarkers to therapeutic targets," Int. J. Mol. Sci. 23(5): 2684 (2022).
Feng et al., "JD419, a *Staphylococcus aureus* Phage With a Unique Morphology and Broad host Range," Front. Microbiol. 12:602902. (2021).
Fujii, "The Pathogenic and Therapeutic Implications of Ceramide Abnormalities in Atopic Dermatitis," Cells 10(9): 2386 (2021).
Gordon et al., "A novel pathogenic variant in the corneodesmosin gene causing generalized inflammatory peeling skin syndrome with marked eosinophilia and trichorrhexis invaginate," Pediatr. Dermatol. 39(2): 268-272 (2022).
Ishida-Yamamoto et al., "The biology and regulation of corneodesmosomes," Cell Tissue Res. 360(3): 477-482 (2015).
Ito et al., "Biology of Hsp47 (Serpin H1), a collagen-specific molecular chaperone," Seminar Cell Dev. Biol. 62: 142-151 (2017).
Klein et al., "GRHL3 binding and enhancers rearrange as epidermal keratinocytes transition between functional states," PLOS Genet. 13(4): e1006745 (2017).
Kulišić et al., "Immunohistochemical Analysis of Adhesion Molecules E-Selectin, Intercellular Adhesion Molecule-1, and Vascular Cell Adhesion Molecule-1 in Inflammatory Lesions of Atopic Dermatitis," Life 13: 933 (2021).
Meckfessel et al., "The structure, function, and importance of ceramides in skin and their use as therapeutic agents in skin-care products," J. Am. Acad. Dermatol. 71: 177-184 (2014).
Medic et al., "Differential PAX3 functions in normal skin melanocytes and melanoma cells," Biochem. Biophys. Res. Comm. 411(4): 832-837 (2011).
Mihaylova et al., "Examination of the Antioxidant Activity of *Haberlea rhodopensis* Leaf Extracts and their Phenolic Constituents," J. Food Biochem. 37(3): 255-261 (2011).
Nakahara et al., "Potential role of endothelin-1 in atopic dermatitis," Curr Treat. Options Allergy 6: 156-163 (2019), Abstract.
Nomura et al., "Cytokine milieu of atopic dermatitis, as compared to psoriasis, skin prevents induction of innate immune response genes," J. Immunol. 171(6): 3262-3269 (2003).
Park et al., "A novel endogenous damage signal, CSF-2, activates multiple beneficial functions of adipose tissue-derived mesenchymal stem cells," Mol. Therapy 27(6): 1087-1100 (2019).
Peng et al., "Identifying the Potential Therapeutic Targets for Atopic Dermatitis Through the Immune Infiltration Analysis and Construction of a ceRNA Network," Clin. Cosmet. Investig. Dermatol. 14:437-453 (2021).
Preethi et al., "Antioxidant Potential of an Extract of *Calendula officinalis*. Flowers in Vitro. and in Vivo.," Pharmaceutical Biology. 44(9): 691-697 (2006).
Raskin et al., "Can an apple a day keep the doctor away?," Current Pharmaceutical Design. 10, 3419-3429 (2004).
Revilla et al., "Comparison of Several Procedures Used for the Extraction of Anthocyanins from Red Grapes," J. Agric. Food Chem. 46: 4592-4597 (1998).
Salminen, "Aryl hydrocarbon receptor (AhR) reveals evidence of antagonistic pleiotropy in the regulation of the aging process," Cell. Mol. Life Sci. 79: 489 (2022).
Seigner et al., "A *Symphytum officinale* Root Extract Exerts Anti-inflammatory Properties by Affecting Two Distinct Steps of NF-kB Signaling," Frontiers in Pharmacology 10: 289 (2019).

(56) References Cited

OTHER PUBLICATIONS

Serveaux-Dancer et al., "Pathological Implications of Receptor for Advanced Glycation End-Product (AGER) Gene Polymorphism," Dis. Markers 2019: 6067353 (2019).

Sowa et al., "Proliferative and antioxidant activity of *Symphytum officinale* root extract," Natural Product Research 32(5): 605-609 (2017).

Tallarida et al., "Quantitative methods for assessing drug synergism," Genes & Cancer 2(11): 1003-1008 (2011).

Tsybikov et al., "Plasma endothelin-1 levels during exacerbation of atopic dermatitis," Allergy Asthma Proc. 36(4): 320-324 (2015).

Tyavambiza et al., "Cellular and Molecular Events of Wound Healing and the Potential of Silver Based Nanoformulations as Wound Healing Agents," Bioengineering 9(11): 712 (2022).

Wagener et al., "Targeting the redox balance in inflammatory skin conditions," Int. J. Mol. Sci. 14(5): 9126-9167 (2013).

Werfel, "The role of leukocytes, keratinocytes, and allergen-specific IgE in the development of atopic dermatitis," J. Invest. Dermatol. 129(8): 1878-1891 (2009).

Zheng et al., "A novel function of NLRP3 independent of inflammasome as a key transcription factor of IL-33 in epithelial cells of atopic dermatitis," Cell Death Disease 12: 871 (2021).

U.S. Appl. No. 18/641,861, filed Apr. 22, 2024.

Non-Final Office Action in U.S. Appl. No. 18/641,861, dated Aug. 23, 2024.

Final Office Action in U.S. Appl. No. 18/641,861, dated Dec. 5, 2024.

Notice of Allowance in U.S. Appl. No. 18/641,861, dated Jul. 7, 2025.

Dell'Acqua et al., "Skin benefits of a myconoside-rich extract from resurrection plant Haberlea rhodopensis," *International Journal of Cosmetic Science* 34(2):132-139 (2012).

International Search Report and Written Opinion in International Application No. PCT/US2025/048117, dated Jan. 22, 2026.

* cited by examiner

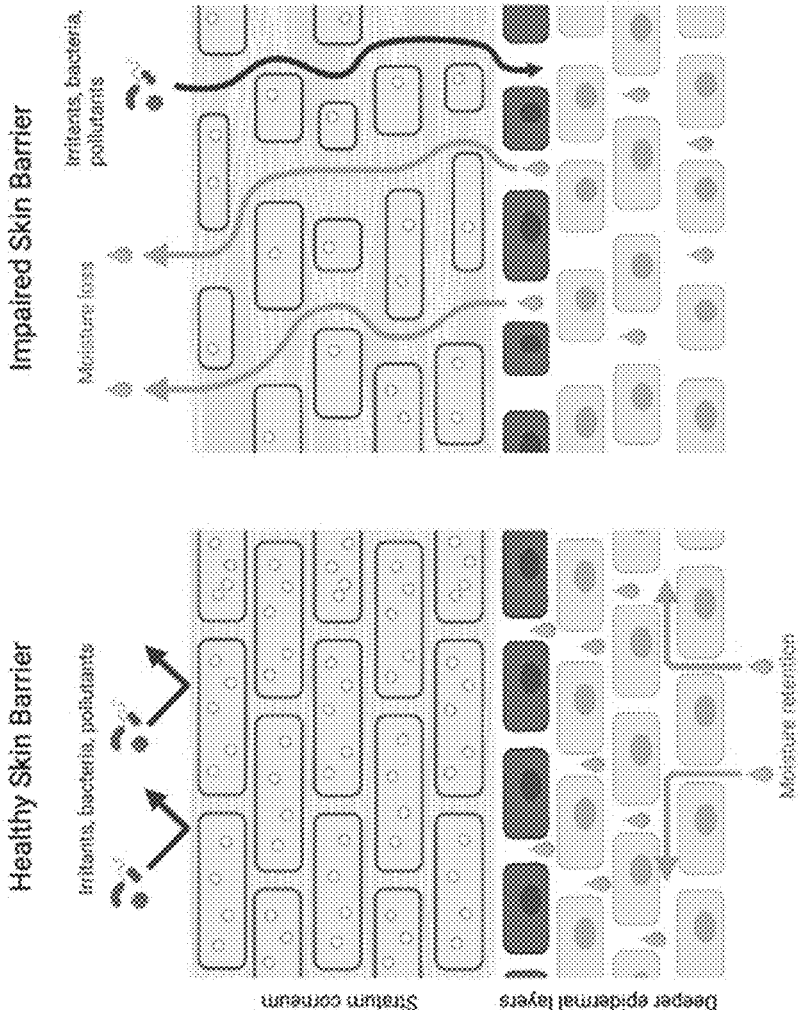

COMPOSITIONS AND METHODS FOR AMELIORATING SYMPTOMS ASSOCIATED WITH INFLAMMATORY SKIN DISORDERS

FIELD OF THE INVENTION

The present invention generally relates to compositions and methods for treating and managing inflammatory skin disorders such as dermatitis. More particularly, the present invention provides ways for effectively treating and managing inflammatory skin disorders by addressing their symptoms which include a structurally impaired stratum corneum (SC), skin inflammation, itchiness, burning, formation of lesions, and oxidative stress.

BACKGROUND OF THE INVENTION

Skin represents the body's first line of defense against external/environmental insults that would otherwise damage sensitive underlying tissue and organs. In addition, it also functions as a relatively water-impermeable barrier that keeps water/moisture from prematurely escaping from the body. This barrier is subject to numerous extrinsic and intrinsic negative factors that affect its appearance, physical properties, and physiological functions. Extrinsic factors include ultraviolet radiation, environmental pollution, heat, harsh surfactants, lifestyle (such as diet, exercise, or sleep quality) and mechanical stress caused by, for example, shaving or garment friction and the like. Intrinsic factors include chronological aging, a person's genetic makeup, and other biological conditions such as dermatitis, psoriasis, acne vulgaris, and Hidradenitis Suppurativa (HS).

The skin is divided into two main structural layers: the epidermis and the dermis. The vital barrier function of the skin resides primarily in the top stratum of the epidermis, the stratum corneum (SC), a.k.a. the skin barrier. The epidermis also has immunologic functions and provides some protection from UV light via its pigment system. The predominant cell type of the epidermis is the keratinocyte which represents approximately 90% of the cells comprising the epidermis. They originate in the deepest layer of the epidermis (stratum basal) and migrate up to the final barrier layer, the stratum corneum.

Keratinocytes proliferate in the basal layer and start differentiating on their way to the surface. During this process, they significantly change their morphology and start to produce keratin, cytokines, growth factors, and interleukins. They play an essential role in protection as they form a tight barrier that prevents foreign substances, including pathogens, from entering the body, while minimizing the loss of moisture, heat, and other constituents. These cells have a structural role, forming tight bonds with other cells in the epidermis and maintaining them in their locations. In addition, keratinocytes function as immunomodulators following skin injuries. At each stage of differentiation, keratinocytes express not only specific keratins, but various biological markers as well such as involucrum, loricrin, transglutaminase, filaggrin, and caspase.

In addition to their structure-forming properties, keratinocytes also interact with other skin cells such as fibroblasts, melanocytes, lymphocytes, and Langerhans cells. Crosstalk between keratinocytes and fibroblasts is essential for maintaining skin homeostasis and for ensuring a balanced wound-healing process. These two cell types communicate via paracrine signaling mechanisms, the disruption of which can lead to the presence of chronic wounds. The interaction between keratinocytes and melanocytes is also critically important for skin barrier homeostasis. Melanocytes produce melanin which absorbs UV light and prevents DNA damage to the keratinocytes which, in turn, stimulate melanocyte functions such as proliferation, differentiation, and melanogenesis. Keratinocytes also possess immunomodulatory functions that interact with lymphocytes and Langerhans cells in the skin.

Keratinocytes also play a role in wound-healing via a process known as re-epithelialization, necessary for successful wound closure. When the skin is injured, keratinocytes are activated and migrate to the wound where they start proliferating to fill/close the wound. During wound healing, interactions between keratinocytes, fibroblasts, and immune cells are critically important to the healing process.

When the skin barrier is compromised (i.e., structurally impaired) or when pathogens enter the skin, an inflammatory response is triggered. Keratinocytes actively participate in this process by expressing cytokines that transmit positive or negative signals to immune cells. They also play a role in inflammatory skin conditions like dermatitis and psoriasis by recruiting and activating dendritic cells and leukocytes.

Corneocytes are essentially "dead" keratinocytes, i.e., they are devoid of nuclei and cytoplasmic organelles. They are primarily comprised of the protein keratin and are continually shed (desquamated) and renewed from lower epidermal layers, a process commonly referred to as cell turnover.

The skin barrier is often analogized to a brick wall. The corneocytes with their resistant cell envelopes and keratin microfibrils are the bricks, whereas the layers of lipids found between the cells are the mortar. This lipid mortar is the main barrier to water prematurely escaping via the stratum corneum. Both the bricks and mortar of the stratum corneum are produced by keratinocytes at the stratum granulosum where keratinocytes release the lipids (mortar) into the spaces between the cells as they are being transformed into the corneocytes (bricks). Two proteins from the keratohyalin granules, filaggrin and loricrin, play key roles in the formation of the corneocytes. Filaggrin is an acronym for filament-aggregating protein, which is derived from profilaggrin whose production is predominantly controlled by the filaggrin (FLG) gene.

The lamellar bodies that appear at the stratum granulosum contain lipids which are released into the intercellular spaces as the stratum corneum forms. The lipids are comprised of glucosyl ceramides, cholesterol esters, and long-chain fatty acids. In the intercellular space, the glucosyl ceramides are converted to ceramides. The lipids spontaneously organize into multiple layers between the stratum corneum cells.

This lipid mortar is critically important to skin barrier function, with ceramides being vital to the organization and functioning of the barrier. The lamellar bodies of the stratum corneum release other important molecules into the inter-corneocyte spaces in addition to the lipids that form the permeability barrier. The proteolytic enzymes involved in desmosome hydrolysis as well as inhibitors of those enzymes to control rates of desquamation are released by the lamellar bodies, as are antimicrobial peptides called "defensins", which play a role in protecting the skin from infection. Production of these peptides is increased in skin with psoriasis, but not in skin suffering from atopic dermatitis (dermatitis). This is believed to account for the increased susceptibility of dermatitis sufferers to skin infection and dermatitis-prone skin may be more likely to spread nosocomial infections.

The very specialized bricks and mortar of the stratum corneum work together to produce a covering for the skin that is both flexible and protective. When functioning properly, it defends the body against dehydration, external toxins, and bacterial assault, while protecting the more fragile keratinocytes below from mechanical disruption.

FIG. 1 depicts how the skin barrier functions when healthy vs. when impaired. As can be seen in FIG. 1, a breakdown of the skin barrier results from a breakdown in the tight adhesion of the cells in the SC, and the loss of intercellular lipids (e.g.: ceramides) thereby allowing excess egress of moisture and pronounced ingress of pathogens. What is not so clear is whether the breakdown of the skin barrier is initially caused by external/environmental influences (e.g. UV rays, pollution) or by internal influences (e.g., cytokines, chemokines and reactive oxidative stress (ROS)) residing below the epidermis.

Atopic dermatitis (AD) is a common inflammatory skin disorder. While the precise cause of AD is currently unknown, its pathophysiology is influenced by a complex interplay between skin barrier dysfunction, inflammation, genetics, and environmental factors. This pathophysiology can be reduced to a basic description which generally consists of three fundamental steps, though not necessarily in this precise order given the two competing theories for the genesis of these diseases. In the "outside-in" hypothesis, epidermal barrier dysfunction triggers immune activation; in contrast, based on the "inside-out" hypothesis, dermatitis is primarily cytokine driven with secondary skin barrier dysfunction.

The modern approach to defining dermatitis pathogenesis appears to now be centered on integrating these two mechanisms and is oriented toward characterizing their interplay in AD as it is not clear which individual model is implicated or whether a combination of the two models explains the disease process. (Facheris, P., Jeffery, J., Del Duca, E. et al. The translational revolution in atopic dermatitis: the paradigm shift from pathogenesis to treatment. *Cell Mol Immunol* 20, 448-474 (2023). doi.org/10.1038/s41423-023-00992-4.)

Myriad central genetic mutations have been demonstrated in the pathogenesis of AD: mutations in structural epidermal barrier proteins, mutations in functional proteins that maintain the epidermal barrier, and mutations in factors that regulate the immune system. Skin barrier alterations, with dysfunction of barrier-related proteins such as filaggrin (FLG), loricrin (LOR), and involucrin (IVL), are the first steps that explain the subsequent sensitization against allergens and the so-called "atopic march" in the "extrinsic" form of AD, where the extrinsic form of AD has a signature increase in total serum IgE levels. Alteration of the skin barrier is also related to alteration of the inter-corneocyte lipid composition (e.g. ceramides), with further trans-epidermal water loss (TEWL). This, in turn, contributes to the skin dryness typical of AD patients and increased penetration of allergens and pathogens creating a feedback loop.

Skin barrier dysfunction in AD is characterized by a lower expression of terminal differentiation markers, such as filaggrin (FLG) and loricrin (LOR), and by a higher permeability defect caused by skin lipid film impairment and higher trans-epidermal water loss. This makes AD skin more prone to the penetration of external agents (antigens, allergens, pollution, etc.) that are harmful to keratinocytes. Damaged keratinocytes produce epidermal alarmins such as IL-33, IL-25, and TSLP, which activate the dendritic cells (DCs) and type 2 innate lymphoid cells (ILC2s) that produce IL-5 and IL-13, which activate eosinophils and Th2 cells. Local Th2 polarization, in return, further diminishes barrier functions and sustains itching, causing skin barrier impairment and facilitating dysbiosis. AD skin shows a higher proliferation of the members of the genus *Staphylococcus*, especially *S. aureus*, which can further damage keratinocytes and sustain local inflammation." (Facheris, P., Jeffery, J., Del Duca, E. et al. The translational revolution in atopic dermatitis: the paradigm shift from pathogenesis to treatment. *Cell Mol Immunol* 20, 448-474 (2023). doi.org/10.1038/s41423-023-00992-4.)

Conversely, while sharing a similar Th2 signature, "intrinsic" AD is characterized by increased Th1 expression in the blood compared to extrinsic AD and lower CCL17 levels. Intrinsic AD also shows greater cellular infiltrates with T cells, Langerhans cells, and myeloid DCs. Th17- and Th22-driven expression of the antimicrobials S100A9 and S100A12 was found to be higher in intrinsic AD, with Th17 expression positively correlating with disease severity. (Facheris, P., Jeffery, J., Del Duca, E. et al. The translational revolution in atopic dermatitis: the paradigm shift from pathogenesis to treatment. *Cell Mol Immunol* 20, 448-474 (2023). doi.org/10.1038/s41423-023-00992-4.)

The microenvironment of a compromised skin barrier contributes, especially in the acute phase, to the activation of the immune system with a predominantly, but not exclusively Th2-mediated reaction and the release of proinflammatory cytokines and chemokines. On the other hand, this process may occur in the opposite order with proinflammatory processes leading to a disturbed skin barrier. Either way, these cytokines and chemokines include alarmins such as tumor necrosis factor (TNF) and interleukins (IL-4, IL-9, IL-22). Epithelium-derived cytokines, such as thymic stromal lymphopoietin (TSLP), IL-25 and IL-33 also act as alarmins after appropriate stimulation, including oxidative stress (OS), and activate a Th2-mediated response in AD, contributing to the inflammatory state of the skin.

The persistence of Th2 inflammation and skin barrier disruption contributes to inflammation and to the overproduction of reactive oxygen species (ROS), such as superoxide and hydrogen peroxide. In addition to this mechanism, the increase in ROS may also depend on other exogenous factors such as solar radiation, pollution, psychological stress, and infections. For example, *Staphylococcus aureus*, a pathogen that frequently causes skin infections and flares up in patients with AD because of a disruption in the skin barrier such as in the case of filaggrin deficiency, can sustain skin inflammation through ROS released by monocytes activated by the pathogen itself. Over time, the accumulation of ROS can eventually cause oxidative stress due to an imbalance between the generation of excess ROS and the body's ability to produce ROS-neutralizing antioxidants.

Inflammatory skin disorders characterized by itch as the primary symptom encompass a wide range of conditions, each with its unique underlying causes and manifestations. These disorders, collectively referred to as inflammatory itch disorders, often present with intense itching sensations, leading to significant discomfort and distress for affected individuals. Conditions such as atopic dermatitis, psoriasis, and allergic contact dermatitis are prime examples of inflammatory skin disorders where itch plays a central role. The itching sensation associated with these conditions can be relentless, interfering with daily activities, disrupting sleep patterns, and negatively impacting quality of life. Despite varying etiologies, these disorders share common inflammatory pathways that contribute to the perception of itch, including activation of immune cells, release of proinflammatory mediators, and alteration in nerve signaling within the skin.

One key player in the pathogenesis of inflammatory itch disorders, particularly in children, is the gene interleukin-13 (IL-13). IL-13 is a cytokine, i.e., a small protein involved in cell signaling, that plays a crucial role in regulating immune responses and inflammation. In the context of inflammatory skin conditions, IL-13 has been implicated in promoting the inflammatory cascade that triggers the itch sensation. Research has shown that elevated levels of IL-13 are present in the skin of individuals with conditions like atopic dermatitis, where itch is a predominant symptom.

Genetic studies have identified variation in the IL-13 gene that may predispose individuals, especially children, to develop inflammatory skin disorders characterized by severe itching. The overproduction of IL-13 triggers a cascade of events within the skin, including the recruitment of immune cells and the release of itch-inducing molecules, ultimately leading to heightened itch perception and exacerbation of the underlying skin inflammation.

In individuals suffering from inflammatory disorders such as dermatitis and psoriasis, not only is their skin barrier compromised leading to increased trans epidermal water loss (TEWL) and enhanced susceptibility to skin irritants and allergens, but so too is their skin's microbiome. In the case of dermatitis, there is often a reduced diversity of microbial species and an overgrowth of certain harmful bacteria such as *Staphylococcus aureus*. More particularly, during AD flare-ups, the loss of microbiome diversity towards an overgrowth of *S. aureus* correlates with disease severity. *S. aureus* strains isolated from AD lesions have been shown to produce a variety of toxins and enzymes with aggressive cell-damaging and inflammation-inducing properties. *S. aureus* directly damages keratinocytes by adhering to cells and forming transmembrane pores through the secretion of staphylococcal toxin ultimately leading to the breakdown of cellular ATP metabolism. *S. aureus* superantigens elicit the production of IgE antibodies, levels of which correlate with disease severity. This imbalance, known as dysbiosis, exacerbates inflammation and thereby contributes to the severity of dermatitis symptoms.

When it comes to treatment options, topical corticosteroids are overwhelmingly the most frequently prescribed class of drugs for atopic dermatitis. However, long-term application of topical corticosteroids is not recommended because of the risk of skin atrophy, dyspigmentation, acneiform eruptions, and risks associated with systemic absorption such as Cushing's disease. Topical calcineurin inhibitors are generally effective and safe as short-term treatments, but concerns of skin malignancies and increased risk of lymphomas have prompted regulatory authorities to require a warning regarding their long-term safety.

First generation antihistamines are widely prescribed for acute symptomatic treatment of pruritus, although their effectiveness is limited and largely attributed to their sedating effect. Oral immunosuppressants and glucocorticoids are effective but are sometimes associated with severe toxicity and side effects, thus limiting their use to short courses and/or intermittent therapy. No systemic agents are approved in the treatment of atopic dermatitis in children. All systemic agents are used off label (cyclosporine, methotrexate, etc.) and have a broad immunosuppressive effect which predisposes the patients to serious infections and increased risk of malignancies if used for prolonged periods. Other reported significant side effects with these agents include gastritis, stunted growth, diabetes, weight gain, hypertension, osteoporosis, and adrenal suppression (corticosteroids), elevated liver enzymes and leukopenia. Moreover, a high proportion of patients in which the condition is initially controlled by systemic agents suffer from relapse once therapy is discontinued. As a result, there exists a significant unmet need for alternative compositions and methods for managing inflammatory skin conditions such as dermatitis and psoriasis.

Based on the foregoing, it is an object of the present invention to provide compositions and methods capable of addressing the symptoms associated with chronic inflammatory skin disorders which include at least one of the following: (i) a compromised/structurally degraded skin barrier, (ii) inflammation caused by the activation of the body's immune system and its release of proinflammatory cytokines, (iii) itching sensation, (iv) burning sensation, (v) formation of lesions on the skin surface, and (vi) oxidative stress, in order to effectively treat and manage such disorders.

It is also an object of the present invention to provide methods of treating and managing inflammatory skin disorders by effectively addressing the above-referenced symptoms.

SUMMARY OF THE INVENTION

According to certain aspects of the present invention, compositions and methods are provided for treating and managing symptoms associated with inflammatory skin disorders such as dermatitis and psoriasis.

According to one embodiment, the present disclosure provides a topical skincare composition containing: (1) a synergistic blend of at least: (a) *Calendula officinalis* plant or stem cell extract; (b) *Symphytum officinale* extract; (c) a *Haberlea rhodopensis* extract, e.g., a biotech-derived *Haberlea rhodopensis* extract; (d) *Padina pavonica thallus* extract; and (2) at least one skin protectant active ingredient, wherein the composition is capable of effectively treating and managing symptoms associated with inflammatory skin disorders such as dermatitis and psoriasis.

In some embodiments, (a) is present in an amount of from about 0.1 to about 5% by weight, (b) is present in an amount of from about 0.1 to about 5% by weight, (c) is present in an amount of from about 0.1 to about 5% by weight, (d) is present in an amount of from about 0.1 to about 5% by weight; and (2) is present in an amount of from about 0.01 to about 5% by weight, all weights based on total weight of the composition.

In some embodiments, (a) is present in an amount of from about 0.5 to about 4% by weight, (b) is present in an amount of from about 0.1 to about 4% by weight, (c) is present in an amount of from about 0.5 to about 4% by weight, (d) is present in an amount of from about 0.5 to about 4% by weight; and (2) is present in an amount of from about 0.02 to about 3% by weight, all weights based on total weight of the composition.

In some embodiments, (a) is present in an amount of from about 1 to about 3% by weight, (b) is present in an amount of from about 0.4 to about 3% by weight, (c) is present in an amount of from about 0.75 to about 2% by weight, (d) is present in an amount of from about 1 to about 3% by weight; and (2) is present in an amount of from about 0.5 to about 2% by weight, all weights based on total weight of the composition.

In some embodiments, the composition further includes at least one humectant. In some embodiments, the at least one humectant is present in an amount of from about 0.1 to about 10% by weight, or from about 4 to about 8% by weight, based on total weight of the composition. In some embodiments, the at least one humectant is hyaluronic acid.

In some embodiments, the composition further includes at least one ceramide. In some embodiments, the ceramide is present in an amount of from about 0.01 to about 0.5% by weight, or from about 0.02 to about 0.3% by weight, based on total weight of the composition.

In some embodiments, the present disclosure provides a method of treating and managing symptoms associated with inflammatory skin disorders, comprising applying the composition described herein onto skin of a subject in need thereof. In some embodiments, the symptoms include at least one of a compromised skin barrier, inflammation, itchiness sensation, burning sensation, formation of lesions, and oxidative stress.

In some embodiments, the method further includes oral administration of a dietary supplement comprising at least: (a) *Buddleja globosa* leaf extract; (b) *Aristotelia chilensis* leaf extract; (c) *Ugni molinae* leaf extract; and (d) L-histidine.

In some embodiments, the method may also include cleansing skin with a microbiome-friendly cleansing product prior to applying the topical composition onto the skin.

In some embodiments, the method may further include applying a bacteriophage topical product that is designed to kill different *S. aureus* species. The bacteriophage will preferably be applied onto the skin prior to application of the composition of the present disclosure.

According to yet another embodiment, the method further includes orally administering a synbiotic supplement comprising a therapeutically effective amount of: (a) a probiotic blend of bacterial components comprising at least: (i) *Lactobacillus helveticus*, (ii) *Lactobacillus plantarum*, (iii) *Bifidobacterium longum*, and (iii) *Streptococcus thermophilus*; and (b) at least one plant-based, antioxidant-rich source of fiber.

In yet another embodiment, the method of the present disclosure further includes topical application of a probiotic serum comprising live *Lactobacillus plantarum* lactobacilli.

Other embodiments of the present disclosure will become apparent from a review of the ensuing detailed disclosure.

BRIEF DESCRIPTION OF THE DRAWINGS

To describe the manner in which the above-recited and other advantages and features of the disclosure can be obtained, a more particular description of the disclosure briefly described above will be rendered by reference to specific embodiments thereof, which are illustrated in the appended drawings.

FIG. 1 depicts the functioning of a healthy skin barrier versus a structurally damaged one. FIG. 1 is from www.elysiumhealth.com/blogs/aging101/what-is-the-skin-barrier.

DETAILED DESCRIPTION

For purposes of the present disclosure, the use of the term "inflammatory skin disorders" is intended to encompass those disorders whose symptoms include at least one of: a structurally impaired skin barrier; inflammation; itchiness sensation; burning sensation; formation of lesions, and oxidative stress. Examples include dermatitis, psoriasis, and hidradenitis suppurativa.

Compositions of the present disclosure can comprise, consist essentially of, or consist of, the components of the present disclosure as well as other ingredients described herein. The term "comprising" as used herein is meant to include various optional, compatible components that can be used in the preservative systems and cosmetic compositions of the present disclosure without limiting the inclusion, use of, or cooperation with other ingredients, excipients, uses, or otherwise. The term "consisting essentially of" as used herein means that the composition or component may include additional ingredients, but only if the additional ingredients do not materially alter the basic and novel characteristics of the compositions or methods.

As used herein, the words "preferred," "preferably," and variants thereof refer to embodiments of the disclosure that afford certain benefits under certain circumstances. However, other embodiments may also be preferred under the same or other circumstances. Furthermore, the recitation of one or more preferred embodiments does not imply that other embodiments are not useful and is not intended to exclude other embodiments from the scope of the disclosure.

Numerical ranges as used herein are intended to include every number and subset of numbers contained within that range, whether specifically disclosed or not. Further, these numerical ranges should be construed as providing support for a claim directed to any number or subset of numbers within that range.

All percentages, parts, proportions, and ratios as used herein are by weight of the total composition, unless otherwise specified. All such weights as they pertain to listed ingredients are based on the active level.

All references to singular characteristics or limitations of the present disclosure shall include the corresponding plural characteristic or limitation, and vice versa, unless otherwise specified or clearly implied to the contrary by the context in which the reference is made.

All publications, articles, papers, patents, patent publications, and other references cited herein are hereby incorporated in their entireties for all purposes to the extent consistent with the disclosure herein.

The term "oxidative stress" as described herein refers to the disturbance in balance between reactive oxygen species (ROS) and antioxidants present in the skin caused by extrinsic and/or intrinsic factors. Extrinsic factors include, for example, exposure to UV radiation, high energy visible light, pollution, and products containing harsh chemicals. Intrinsic factors include, for example, chronological aging, a person's genetic makeup, and other biological changes that occur from within the skin such as atopic dermatitis, psoriasis, acne vulgaris, and hidradenitis suppurativa.

The term "consistently applying" as described herein refers to an individual suffering from inflammatory skin disorders incorporating the composition of the present disclosure into their skincare regimen.

The term "microbiome-friendly" as described herein refers to a product which is capable of preserving microbial population, diversity and balance on the skin.

The term "bacteriophage" as used herein refers to those viruses capable of killing *Staphylococcus aureus* (*S. aureus*) bacterium.

As used herein, "treatment" or "treating" means the alleviation, prophylaxis or reversal of a condition, a disease, or a disorder, or at least a discernible symptom thereof. In one embodiment, "treatment" or "treating" refers to a mitigation, prophylaxis, or reversal of at least one measurable physical parameter related to the condition, disease, or disorder being treated, not necessarily discernible in or by the individual being treated. In yet another embodiment, "treatment" or "treating" refers to inhibiting or slowing the progression of a condition, a disease, or a disorder, either physically, e.g., stabilization of a physiologically discernible symptom, e.g., stabilization of a physical parameter, or both.

In yet another embodiment, "treatment" or "treating" refers to delaying the onset of a condition, disease, or disorder.

As used herein, the term "probiotics" is defined as substances which stimulate the growth of microorganisms, especially those with beneficial properties that give health benefits to the host when orally administered in an appropriate amount. Their established safety and beneficial effects on human health have led to the emergence of probiotics as substitutes or complements to medicines. The advantage of probiotics is that they have very few side effects.

The term "prebiotics" typically refers to foods having a high fiber content which can act as a food source for human microflora.

As used herein, the term "synbiotics" refers to dietary supplements comprised of both prebiotic and probiotic ingredients, the combination of which ha immunomodulating and gastrointestinal flora-restoring activity.

It has surprisingly and unexpectedly been discovered by the inventors that a combination of: (a) *Calendula officinalis* extract; (b) *Symphytum officinale* extract; (c) *Haberlea rhodopensis* extract, (d) *Padina pavonica thallus* extract, and (e) at least one skin protectant active ingredient, when applied onto skin, has a synergistic influence on the skin barrier and, in particular, certain genes that are known to help manage oxidative stress, restore skin barrier structure and integrity, reduce inflammation, restore skin barrier homeostasis, and support wound healing and tissue remodeling. The synergistic influence on these genes facilitates the effective treatment and management of certain symptoms associated with inflammatory skin disorders such as dermatitis, psoriasis, seborrheic dermatitis, and hidradenitis suppurativa.

*Calendula officinalis* extract is derived from the cells of the marigold plant. Common bioactive compounds found therein include, for example, flavonoids, phenolic acids, carotenoids, triterpenic alcohols, polycarbohydrates, proteins, amino acids, saturated hydrocarbons, vitamin C, and mineral substances. One example of the type of *Calendula officinalis* extract used by the present disclosure is commercially available from Innova BM, a company headquartered in Bulgaria, which sells the extract under the tradename Innova Stem Cell *Calendula* W®.

In some embodiments, the *Calendula officinalis* extract is a stem cell extract. The *Calendula officinalis* stem cell extract of the present disclosure may be employed in an amount of from about 0.1 to about 5% by weight, including from about 0.5 to about 4% by weight, or from about 1 to about 3% by weight, or from about 2 to about 3% by weight, all weights based on the total weight of the composition. The *Calendula officinalis* extract is employed in the form of an oil infusion derived from either a plant macerate or plant stem cells grown in a bioreactor. The biotech method employed by Innova BM uses an in-vitro cell culture of *Calendula officinalis* cells to create a sustainable, eco-friendly cell extract containing a higher concentration of beneficial phyto-chemicals.

*Symphytum officinale* extract comprises the primary bioactive compounds found in *Symphytum officinale*, including allantoin, rosmarinic acid and ellagic acid.

The *Symphytum officinale* extract of the present disclosure may be employed in an amount of from about 0.1 to about 5% by weight, including from about 0.1 to about 4% by weight, or from about 0.4 to about 3% by weight, or from about 0.4 to about 2% by weight, all weights based on the total weight of the composition. In some embodiments, the *Symphytum officinale* extract is employed in the form of an oil infusion derived from either a plant macerate or plant stem cells grown in a bioreactor. The biotech method uses an in-vitro cell culture of *Symphytum officinale* cells to create a sustainable, eco-friendly cell extract containing a higher concentration of beneficial phyto-chemicals. One example of the type of *Symphytum officinale* extract used in the present disclosure is commercially available from O&3, headquartered in England, in the form of an oil infusion.

*Haberlea rhodopensis* is a tertiary relict plant endemic to the Balkan region, especially the Rhodope mountains in Bulgaria. In some embodiments, the *Haberlea rhodopensis* extract of the present disclosure is employed in the form of an oil infusion generated from either a plant macerate or plant stem cells grown in a bioreactor. A *Haberlea rhodopensis* extract produced from plant macerate or plant stem cells grown in a bioreactor is referred to herein as a "biotech-derived *Haberlea rhodopensis* extract."

The *Haberlea rhodopensis* extract of the present disclosure may be employed in an amount of from about 0.1 to about 5% by weight, including from about 0.5 to about 4% by weight, or from about 0.75 to about 2% by weight, all weights based on the total weight of the composition.

One example of the type of *Haberlea rhodopensis* extract used in the present disclosure is commercially available from various suppliers including, for example, Innova BM, a company headquartered in Bulgaria, under the tradename InnovaBio Tech *Haberlea*®. The biotech method employed by Innova BM uses an in-vitro cell culture of *Haberlea rhodopensis* cells cultivated from the plant to create a sustainable, eco-friendly cell extract containing a higher concentration of beneficial phyto-chemicals.

*Padina pavonica thallus* extract is derived from a brown alga found in the Mediterranean Sea. The algal extract is typically obtained from an aqueous based extraction under pressure. This ingredient is commercially available from Biosil Technologies, Inc., a company headquartered in Allendale, NJ, under the tradename Ocea Health®. The *Padina pavonica thallus* extract of the present disclosure may be employed in an amount of from about 0.1 to about 5% by weight, or from about 0.5 to about 4% by weight, or from about 1 to about 3% by weight, all weights based on the total weight the composition.

Examples of suitable skin protectant active ingredients which may be employed include those found in the FDA's OTC Monograph M016, the entire contents of which is hereby incorporated by reference. An example of a preferred skin protectant active ingredient is colloidal oatmeal.

The skin protectant active ingredient of the present disclosure may be employed in an amount of from about 0.01 to about 5% by weight, or from about 0.02 to about 3% by weight, or from about 0.5 to about 2% by weight, all weights based on the total weight the composition.

According to another embodiment of the present disclosure, the composition further includes at least one humectant. In some embodiments, the humectant provides enhanced hydration and moisturization to de-hydrated skin effected by an inflammatory skin disorder. The humectant may be employed in an amount of from about 0.05 to about 10% by weight, from about 0.1 to about 10% by weight, or from about 4 to about 8% by weight, all weights based on the total weight of the composition. Examples of suitable humectants include, but are not limited to, hyaluronic acid and its derivatives such as sodium hyaluronate, hydrolyzed sodium hyaluronate, and hydrolyzed hyaluronic acid, lecithin, aloe vera, panthenol, glycerin, and seaweed. A particularly preferred humectant for use in embodiments of the present disclosure is hyaluronic acid. In some embodiments, the humectant is hydrolyzed hyaluronic acid, sodium hyaluronate, hydrolyzed sodium hyaluronate, or a combination thereof.

According to another embodiment of the present disclosure, the composition further includes at least one ceramide. In some embodiments, the ceramide structurally enhances the stratum corneum. Ceramides are a group of natural waxy, fatty substances in the skin, composed of sphingosine and lipids (fatty acids) bonded together. Ceramides make up about 50% of all skin lipids and are manufactured in the lower, living cells of the epidermis. As the cells mature and move to the surface, ceramides are released to the topmost layer, the stratum corneum. In the stratum corneum layer, ceramides combine with cholesterol (another important lipid found in the skin) and fatty acids to form an ordered, tightly packed, layered, sheet-like arrangement between the dead cells. Ceramides and cholesterol protect against moisture loss to keep skin youthful and supple and support the structure of the stratum corneum. Exemplary ceramides include ceramide 1, ceramide 2, ceramide 3, ceramide 4, ceramide 5, ceramide 1A, ceramide 6 II, ceramide AP, ceramide EOP, ceramide EOS, ceramide NP, ceramide NG, ceramide NS, ceramide AS, and ceramide NS dilaurate.

The ceramide may be employed in an amount of from about 0.01 to about 0.5% by weight, from about 0.05 to about 0.5% by weight, from about 0.1 to about 0.5% by weight, or from about 0.2% to about 0.3% by weight, all weights based on the total weight of the composition, it being understood that the ceramide component of the composition may comprise a mixture of two or more different ceramides. In some embodiments, the at least one ceramide is selected from ceramide 1, ceramide 2, ceramide 3, ceramide 4, ceramide 5, ceramide 1A, ceramide 6 II, ceramide AP, ceramide EOP, ceramide EOS, ceramide NP, ceramide NG, ceramide NS, ceramide AS, ceramide NS dilaurate, or a combination thereof.

In yet another embodiment of the present disclosure, the compositions are free of a skin-sensitizing amount of an essential oil. In some embodiments, the compositions have a pH ranging from about 4.5 to about 5.5, and preferably from about 4.8 to about 5.3. In some embodiments, a composition "free of" a particular component means that the composition includes less than about 1% by weight, or less than about 0.8% by weight, or less than about 0.5% by weight, or less than about 0.2% by weight, or less than about 0.1% by weight, or less than about 0.05% by weight, or less than 0.01% by weight of the particular component.

In another embodiment, the present disclosure provides a composition containing: (1) a therapeutic blend of plant-based actives comprising at least: (a) *Calendula officinalis* extract; (b) *Symphytum officinale* extract; (c) *Haberlea rhodopensis* extract; and (d) *Padina pavonica thallus* extract; (2) at least one skin protectant active ingredient; (3) at least one humectant; (4) at least one ceramide; (5) an emulsifier; and (6) a dermatologically acceptable carrier, wherein the composition is capable of effectively treating and managing symptoms associated with dermatitis.

Any ingredient capable of emulsifying the composition may be employed as an emulsifier without departing from the spirit of the invention, so long as it is natural and dermatologically acceptable. Examples thereof include, but are not limited to, glyceryl stearate, cetyl alcohol, sodium stearoyl lactylate, sorbitan olivate, cetearyl olivate, cetearyl alcohol, cetearyl glucoside, sodium cetearyl sulfate, and the like. It is also particularly preferred that the emulsifier be free of palm oil.

The compositions of the present disclosure may be in a wide variety of product forms that include, but are not limited to, solutions, suspensions, lotions, creams, gels, sprays, foams, ointments, and serums.

According to embodiments of the present disclosure, the compositions can also additionally comprise suitable optional ingredients as desired. For example, the composition can optionally include other active or inactive ingredients, provided they do not unacceptably alter the benefits of the composition and do not promote skin sensitization. The precise amount of optional ingredients chosen will be determined by those skilled in the art.

Examples of optional ingredients that may be employed include, but are not limited to, emollients, flavonoids, minerals, chelating agents, pH regulators/buffers, rheology modifiers, phytosterols, vitamin $B_{12}$ compound, vitamin $D_3$ compound, anti-inflammatory agents such as licorice extracts, bisabolol, manjistha extracted from plants in the genus *Rubia*, guggul extracted from plants in the genus *Commiphohra, Quillaja saponaria* extract, kola extract, chamomile, red clover extract, sea whip extract, hibiscus extract, maqui extract, meadowsweet extract, rosemary extract, lucuma extract, sea kale extract, Iceland Moss extract, Saskatoon Berry extract, Siberian *Ginseng* extract, spruce needles extract, birch bark extract, blueberry extract, cranberry extract, yarrow extract, marigold extract, and couch grass extract.

A preferred optional ingredient that may be employed is an emollient such as, for example, squalane and/or hemi-squalane.

Additional ingredients that may be employed in order to further potentiate the invention's efficacy may include, for example, Astrocaryum murumuru seed butter, *Theobroma grandiflorum* seed butter, *Theobroma grandiflorum* seed butter, *Spondias mombin* pulp extract, *Mangifera indica* pulp extract, *Musa sapientum* pulp extract, *Mauritia flexuosa* fruit oil, *Physalis angulata* extract, *Xylityl sesquicaprylate, Vaccinium myrtillus* seed oil, *Cucubita pepo* seed extract, linoleic acid, linolenic acid, *Centella asiatica* leaf extract, *Tamarindus indica* see polysaccharide, *Zanthoxylum bungeanum* fruit extract, fucoidan extract, allantoin, *Lactococcus* ferment lysate, *Bellis perennis* flower extract, *Coffea arabica* seed cake extract, *Coffea arabica* seed oil, cotton seed oil, sunflower seed oil, almond oil, linseed oil, *Pichia* ferment lysate filtrate, and whey protein.

The dermatologically acceptable carrier can encompass a wide variety of forms. In some cases, the solubility or dispersibility of the components in the composition may dictate the form and character of the carrier. Non-limiting examples include simple solutions (e.g., aqueous or anhydrous), dispersions, emulsions and solid forms. In certain embodiments, the dermatologically acceptable carrier is in the form of an emulsion. An emulsion can be generally classified as having a continuous aqueous phase (e.g., oil-in-water and water-in-oil-in-water) or a continuous oil phase (e.g., water-in-oil or oil-in-water). While the oil phase may comprise any vegetable oil, so long as it does not cause skin sensitization, a particularly preferred oil component is sunflower seed oil.

The inventors have surprisingly discovered that the use of sunflower oil enables bioactive compounds present in the composition to effectively penetrate into the skin, without the need of having to use skin-sensitizing essential oils, while still facilitating the desired degree of efficacy. The high concentration of linoleic acid (at least 60%) helps maintain the skin barrier and serve as an emollient to lock in moisture and reduce trans-epidermal water loss (TEWL). Sunflower oil is also rich in vitamin E, an antioxidant that helps protect the skin barrier from external stressors like sun exposure and air pollution, vitamins C and D as well as beta-carotene (pre-cursor to vitamin A) that can combine with fatty acids to promote new skin cell growth and prevent of bacterial infection and omega-6 fatty acids that help reduce redness and smooth roughness. In addition, sunflower oil is safe for people with tree nut allergies. Other vegetable oils that may also be used include, but are not limited to, almond oil, olive oil, jojoba oil, babassu oil, castor oil, coconut oil, corn oil, cotton seed oil, linseed oil, mustard oil, safflower oil, sesame oil, soybean oil, sunflower oil, wheat germ oil, argan oil and marula oil.

According to another embodiment, there is provided a method of treating and managing symptoms associated with dermatitis by applying one of the above-disclosed compositions onto the skin of a subject in need thereof. The symptoms include a compromised skin barrier, inflammation, itchiness sensation, burning sensation, formation of eczematous lesions, and oxidative stress.

According to yet another embodiment, the method of the present disclosure further includes the step of orally administering a dietary supplement comprised of a mixture of: (a) *Buddleja globosa* (matico) leaf extract, (b) *Aristotelia chilensis* (maqui) leaf extract, *Ungi molinae* (murta) leaf extract, and (d) L-histidine.

*Buddleja globosa* leaf extract is derived from the leaves of the orange ball *Buddleja*, also known as "matico," a species of flowering plant endemic to Chile and Argentina. The extract has been found to contain glycosidic flavonoids and phenylethanoids such as verbascoside, iridoids, triterpenoids, and di- and sesquiterpenoids, together with two caffeic acid derivatives. These compounds have shown promise in wound healing due to their ability to promote fibroblast growth, with a strong antioxidant effect. This particular leaf extract is also rich in stigmasterol, an unsaturated plant sterol found in plant oils.

The *Buddleja globosa* leaf extract is preferably employed in an amount of from about 0.1 to about 5% by weight, or from about 0.5 to about 3% by weight, or from about 1 to about 2% by weight, based on the total weight of the dietary supplement composition. In some embodiments, the *Buddleja globosa* leaf extract is present in the dietary supplement composition at an amount of about 0.1 to about 5 mg, or about 0.5 to about 3 mg, or about 1 to 2 mg. This extract is commercially available from N-Active EIRL, under the trade name EthniCare® MATICO.

*Aristotelia chilensis* leaf extract is derived from the leaves of a small dioecious evergreen tree in the Elaeocarpaceae family native to South America in the Valdivian temperate rainforests of Chile, which also goes by the name maqui. The extract has been found to contain high amounts of anthocyanins, indole alkaloids, and flavonoids. These compounds serve as a source of antioxidants that help to neutralize free radicals and protect the skin's DNA.

The *Aristotelia chilensis* leaf extract is preferably employed in an amount of from about 0.5 to about 20% by weight, or from about 1 to about 10% by weight, or from about 2 to about 5% by weight, based on the total weight of the dietary supplement composition. In some embodiments, the *Aristotelia chilensis* leaf extract is present in the dietary supplement composition at an amount of about 0.5 to about 20 mg, or about 1 to about 10 mg, or about 2 to about 5 mg. This extract is commercially available from N-Active EIRL under the trade name EthniCare® MAQUI.

*Ugni molinae* leaf extract is derived from the leaves of a woody evergreen shrub from the myrtaceae family commonly found in Chile and is also known by its Spanish name "murta." The extract has been found to contain various phenolic compounds including gallic acid, catechin, quercetin, myricetin, and kaempferol. These compounds have been found to possess strong antioxidant activity against ROS production, lipid peroxidation, and superoxide anion production.

The *Ugni molinae* leaf extract is preferably employed in an amount of from about 0.1 to about 5% by weight, or from about 0.5 to about 3% by weight, or from about 1 to about 2% by weight, based on the total weight of the dietary supplement composition. In some embodiments, the *Ugni molinae* leaf extract is present in the dietary supplement composition at an amount of about 0.1 to about 5 mg, or from about 0.5 to about 3 mg, or from about 1 to about 2 mg. This extract is commercially available from N-Active EIRL, under the trade name EthniCare® MURTA.

Weight ratios of *Aristotelia chilensis* leaf extract to *Buddleja globosa* leaf extract to *Ugni molinae* leaf extract can range from about 1:1:1 to about 6:1:1, about 1:1:1 to about 5:1:1, about 1:1:1 to about 4:1:1, or about 1:1:1 to about 3:1:1. In some embodiments, the ratio of the *Aristotelia chilensis* leaf extract to *Buddleja globosa* leaf extract to *Ugni molinae* leaf extract is about 1:1:1, about 2:1:1, about 3:1:1, about 4:1:1, about 5:1:1, or about 6:1:1.

All three plant extracts (i.e., *Aristotelia chilensis* leaf extract, *Buddleja globosa* leaf extract, and *Ugni molinae* leaf extract) are derived from plant leaves utilizing a solvent extraction process for recovering the respective leaf extracts. A pre-made blend of all three plant extracts utilized by the invention of the present disclosure is commercially available from N-Active SpA, a Chilean company located in Santiago, Chile under the tradename EthniCare® M3 Powder Plus.

L-histidine is an essential amino acid used by the body in the biosynthesis of proteins. It is a key building block of two key skin barrier components, namely, filaggrin protein that provides structure to the skin barrier and the natural moisturization factor complex that helps attract and retain moisture in skin. L-histidine is commercially available from Fifth Nutrisupply Inc, located in Montclair, California.

The L-histidine may be employed in amounts ranging from about 0.05 to about 10 mg, or from about 0.1 to about 5 mg, or from about 0.2 to about 4 mg, all weights based on the total dry weight of the dietary supplement composition.

According to an embodiment of the present disclosure, the method involves daily application of the topical skincare composition, coupled with daily oral administration of the dietary supplement.

According to yet another embodiment, the method further includes applying a therapeutic amount of a bacteriophage which targets *Staphylococcus aureus* bacterium, onto the skin. In some embodiments, the bacteriophage topical product further complement the invention of the present disclosure. An example of a suitable bacteriophage for use by the present disclosure includes, but is not limited to, *Staphylococcus* phage JD419 as described in Feng et al., *Front. Microbiol.* 12:602902 (2021). The precise amount of bacteriophage used to kill the *Staphylococcus aureus* bacterium present on a person's skin can be determined by those skilled in the art.

The topical bacteriophage is preferably applied onto the skin prior to applying the composition of the present disclosure.

According to yet another embodiment, the method further includes orally administering a synbiotic supplement containing a therapeutically effective amount of: (a) a probiotic blend of bacterial components containing at least: (i) *Lactobacillus helveticus*, (ii) *Lactobacillus plantarum*, (iii) *Bifidobacterium longum*, and (iii) *Streptococcus thermophilus*; and (b) at least one plant-based, antioxidant-rich source of fiber. In some embodiments, the use of this type of synbiotic dietary supplement, in combination with the topical composition of the present disclosure, enables symptoms associated with eczema such as gut inflammation and gut microbiome dysbiosis to be ameliorated, while simultaneously enhancing ceramide production in the skin.

In yet another embodiment, the method of the present disclosure further includes topical application of a probiotic serum containing live *Lactobacillus plantarum* lactobacilli. In some embodiments, application of the probiotic serum helps to reduce skin inflammation and balance the skin microbiome.

EXAMPLES

The following examples as set forth herein are intended for illustrative purposes only and are not intended to limit the scope of the disclosure in any way, as many variations thereof are possible without departing from the spirit and scope of the disclosure. In the examples, all concentrations are listed as weight percent, unless otherwise specified.

positive displacement pipette and were spread evenly on top of the RHE tissues. Sterile distilled water was the negative control. Treated tissues were allowed to incubate overnight. The results of the gene expression testing fell into three distinct categories.

At the end of the incubation RNA was extracted and purified with RNeasy Mini Kit cat. #74104 from Qiagen (Germantown, MD), using a QiaCube Connect robotic station (Qiagen). Purified total RNA was assessed at 260 nm and 280 nm with a Thermo Fisher Scientific (Waltham, MA) NanoDrop™ Lite Spectrophotometer.

cDNA was prepared using a High-Capacity RNA-to-cDNA™ Kit (Applied Biosystems, Thermo Fisher) and the expression of the genes of interest was measured by real-time quantitative PCR with a BioRad iCycler iQ Detection System using PCR primers from Realtimeprimers (Elkins Park, PA) and AzuraView GreenFast qPCR Blue Mix LR available from Azura Genomics (Raynham, MA). Efficiency $\Delta\Delta$Ct method was used for quantification of results, after the normalization of gene expression to HPRT1 and GAPDH (housekeeping genes).

Genes were considered differentially expressed if the p value, as determined by the two-tailed t-test, was <0.10 and the modulation was >1.8. However, if a modulation >10 is measured, the p value may be <0.5 for statistical significance.

The synergistic influence exhibited by the mixture of the present disclosure on certain genes associated with anti-oxidative function, as compared to each individual ingredient, is shown in Table 1, below.

TABLE 1

| Gene | 2% *Calendula officinalis* | | 1% *Symphytum officinale* | | 1% *Haberlea rhodopensis* | | Mixture: 2% *Calendula officinalis* 1% *Symphytum officinale* 1% *Haberlea rhodopensis* | |
|---|---|---|---|---|---|---|---|---|
| | T-Test | Regulation | T-Test | Regulation | T-Test | Regulation | T-Test | Regulation |
| HMOX1 | — | — | — | — | — | — | 0.01 | 2.9 |
| SOD1 | — | — | — | — | — | — | 0.01 | −1.2 |
| GPX1 | — | — | — | — | — | — | 0.0 | −1.5 |
| NQO1 | 0.01 | −25.1 | 0.02 | −3.6 | — | — | 0.09 | 1.2 |

Example 1

*Calendula officinalis* stem cell extract in an amount of 2%, an oil infusion of *Symphytum officinale* extract in an amount of 1%, and a biotech-derived *Haberlea rhodopensis* extract in an amount of 1% were evaluated, both individually and in combination, to determine what, if any, gene expression effects they may indicate, per the below-indicated protocol.

Reconstructed Human Epidermis (RHE) tissues were obtained from ZenBio (Research Triangle Park, NC; lot #RHE051820) and were used immediately. Tissues were transferred to 6 well plates and were equilibrated for an hour in 1 ml of pre-warmed medium/well ZenSkin provided by the ZenBio. Samples of the above ingredients were then added non-diluted, in triplicates at 3 mg/cm² with the In the presence of the mixture, antioxidant genes SOD1 and GPX1 were downregulated and HMOX1/NQO1 were activated to provide a more comprehensive ROS reduction mechanism that not only scavenges ROS but protects skin tissue from damage. See, e.g., Wagener et al., *Int. J. Mol. Sci.* 14(5):9126-9167 (2013). Moreover, HMOX1 counteracts the cytotoxic effects caused by high concentrations of free heme in the dermatititstic lesion and enables the NRF2/HMOX1 axis to mediate anti-inflammatory activity, whereas NQO1 provides NRF2 a target to help detoxify xenobiotic compounds as well as ROS.

The synergistic influence exhibited by the mixture of the present disclosure on certain genes associated with ceramide production, as compared to each individual ingredient, is shown in Table 2, below.

TABLE 2

| Gene | 2% *Calendula officinalis* | | 1% *Symphytum officinale* | | 1% *Haberlea rhodopensis* | | Mixture: 2% *Calendula officinalis* 1% *Symphytum officinale* 1% *Haberlea rhodopensis* | |
|---|---|---|---|---|---|---|---|---|
| | T-Test | Regulation | T-Test | Regulation | T-Test | Regulation | T-Test | Regulation |
| SMPD1 | — | — | — | — | — | — | 0.01 | 1.7 |

Ceramides play a key role in reducing permeability of the skin barrier. In dermatitis, skin lipids may contain less ceramide and ceramide composition may be altered.

SMPD1 was surprisingly upregulated by the mixture to increase ceramide production. The protein encoded by this gene is a lysosomal acid (sphingomyelinase) that converts sphingomyelin to ceramide. See, e.g., Kitatani et al., *Cells* 10(9):2386 (2021).

The synergistic influence exhibited by the mixture of the present disclosure on certain genes associated with skin barrier repair/restructuring, as compared to each individual ingredient, is shown in Table 3, below.

FLG was significantly upregulated (more than the sum of the individual components, indicating synergistic amplification) which is known to increase the production of pro-filaggrin, a pre-cursor to filaggrin, a critically important protein for skin barrier structure, and under produced in those with atopic dermatitis.

LOR was upregulated to produce the skin barrier protein loricrin, which is a major component of the skin's cornified envelope. Links between loricrin and other components of the envelope, like filaggrin, hold the corneocytes together and help give the stratum corneum its structural strength.

TABLE 3

| Gene | 2% *Calendula officinalis* | | 1% *Symphytum officinale* | | 1% *Haberlea rhodopensis* | | Mixture: 2% *Calendula officinalis* 1% *Symphytum officinale* 1% *Haberlea rhodopensis* | |
|---|---|---|---|---|---|---|---|---|
| | T-Test | Regulation | T-Test | Regulation | T-Test | Regulation | T-Test | Regulation |
| CDSN | — | — | — | — | — | — | 0.0 | 3.1 |
| FLG | 0.01 | 13.1 | — | 15.6 | — | — | 0.09 | 41.2 |
| GBA | — | — | 0.03 | −1.8 | — | — | 0.08 | 1.5 |
| LCE3D | — | — | 0.01 | 84.4 | 0.1 | 2.7 | 0.00 | 6.7 |
| LOR | — | — | — | — | — | — | 0.01 | 4.1 |

Skin barrier structure and integrity genes of Table 3, associated with a properly functioning stratum corneum, were significantly upregulated in the presence of the mixture as compared to the individual components, especially FLG which is typically under-expressed in skin suffering from atopic dermatitis. Note that this includes both structural protein genes and binding protein genes.

CDSN codes for corneodesmosin and plays a vital role in the structural and functional integrity of the epidermis and hair follicle integrity by preventing the rupture of corneodesmosome, i.e., the main intercellular adhesive structures in the stratum corneum that are transformed from desmosomes at the most superficial layer of the stratum granulosum of the epidermis. The major compositional distinction as compared to desmosomes is the presence of corneodesmosin in the extracellular portion. CDSN was upregulated by the mixture, thereby enhancing the structural integrity of the stratum corneum through improved adhesion, which is helpful for improving lesions in individuals suffering from AD and psoriasis. See, e.g., Ishida-Yamamoto et al., *Cell Tissue Res.* 360(3):477-482 (2015) and Gordon et al., *Pediatr. Dermatol.* 39(2):268-272 (2022).

GBA, an enzyme involved in ceramide production, was also significantly upregulated (compared to downregulated in comfrey alone) evidencing the ability of the mixture to enhance the structural integrity of the stratum corneum.

LCE3D is a gene that encodes a protein that contributes to the structural stability of the cornified envelope and acts as an antimicrobial peptide in the skin. Among its related pathways is keratinization as it is involved in the formation of corneocytes and skin barrier maintenance. Note that in psoriasis, LCE3B and LCE3C are suppressed or missing. LCE3D is one of several genes that are significantly correlated with the main infiltration cell of atopic dermatitis (AD). See, e.g., Peng et al., *Clin. Cosmet. Investig. Dermatol.* 14:437-453 (2021).

The synergistic influence exhibited by the mixture of the present disclosure on certain genes associated with inflammation reduction, as compared to each individual ingredient, is shown in Table 4, below.

TABLE 4

| Gene | 2% Calendula officinalis | | 1% Symphytum officinale | | 1% Haberlea rhodopensis | | Mixture: 2% Calendula officinalis 1% Symphytum officinale 1% Haberlea rhodopensis | |
|------|--------|------------|--------|------------|--------|------------|--------|------------|
| | T-Test | Regulation | T-Test | Regulation | T-Test | Regulation | T-Test | Regulation |
| EDN1 | 0.16 | 4.3 | 0.07 | 4.7 | — | — | 0.03 | -2.7 |
| ICAM1 | — | — | — | — | — | — | 0.08 | 2.5 |
| IL4 | — | — | — | — | — | — | 0.36 | -49.5 |
| IL8 | — | — | — | — | — | — | 0.15 | 2.1 |
| IRF4 | — | — | — | — | — | — | 0.1 | -1.1 |
| AGER | — | — | — | — | — | — | 0 | -1.8 |
| AHR | — | — | — | — | 0.01 | 1.2 | 0.04 | -1.1 |

Inflammation modulation of atopic dermatitis: AHR/NRF2 also play critical roles in the maintenance of skin homeostasis. Specific disruption of AHR function in the skin has been found to be associated with the pathogenesis of atopic dermatitis. See, e.g., Edamitsu et al., Antioxidants (Basel) 11(2):227 (2022).

AGER was downregulated in the presence of the mixture, evidencing a reduction in the production of cell surface receptors for advanced glycation end-products (RAGE) that can cause an unfavorable proinflammatory state. See, e.g., Serveaux-Dancer et al., Dis. Markers 2019:6067353 (2019) and Budu-Aggrey et al., Nature Comm. 14:6172 (2023).

AHR was downregulated in the presence of the mixture. Without intending to be bound by theory, this downregulation is believed to evidence a reduction in immune mediated skin responses based on AHR's ability to inhibit: (i) autophagy, (ii) extracellular matrix degeneration, and (iii) oxidative stress. See, e.g., Salminen, Cell. Mol. Life Sci. 79:489 (2022).

EDN1 was downregulated in the presence of the mixture, which evidences a reduction in itch response as this gene is associated with the production of endogenous pruritogens [endothelin (ET)-1] in the skin. Elevated plasma ET-1 were significantly correlated with AD clinical severity, itch intensity, and serum IgE levels. See, e.g., Tsybikov et al., Allergy Asthma Proc. 36(4):320-324 (2015) and Nakahara et al., Curr Treat. Options Allergy 6:156-163 (2019).

ICAM1 gene was upregulated in the presence of the mixture, evidencing an increase in endothelial cell activation e.g., Marinovid Kulisid et al., Life 13:933 (2023) and Werfel, J. Invest. Dermatol. 129(8):1878-1891 (2009).

IRF4 gene was downregulated in the presence of the mixture, evidencing a reduction in the inflammatory cascade of NLRP3-mediated IL-33 cytokines such as those triggered in AD lesions, as IRF4 interacts with NLRP3 to control IL-33 expression in epithelial cells. See, e.g., Zheng et al., Cell Disease Death 12:871 (2021).

IL4 gene was significantly downregulated in the presence of the mixture, evidencing a reduced production of the IL-4 cytokine that may impair wound healing by decreasing the production of fibronectin, driving inflammation and barrier disruption by decreasing the expression of genes that contribute to the skin's barrier function and innate immune defense. In addition, IL-4 promotes the differentiation of naïve CD4+ T cells into Th2 cells which, in turn, stimulate the production of several inflammatory cytokines (IL-4, IL-13, IL-5 and IL-19) that are involved in the recruitment of eosinophils, basophils and mast cells and in the release of allergic mediators resulting in itching and burning. See, e.g., Chiricozzi et al., Immunotargets Ther 9:151-156 (2020).

IL8 gene was upregulated in the presence of the mixture, evidencing production of the IL-8 cytokine that is an attractant for neutrophils and T-cells and stimulates the migration of keratinocytes for wound healing. IL-8 is typically suppressed in patients with AD because it is inhibited by TH2 cytokines. See, e.g., Nomura et al., J. Immunol. 171(6):3262-3269 (2003) and Fania et al., Int. J. Mol. Sci. 23(5):2684 (2022).

The synergistic influence exhibited by the mixture of the present disclosure on certain genes associated with skin barrier homeostasis, as compared to each individual ingredient, is shown in Table 5, below.

TABLE 5

| Gene | 2% Calendula officinalis | | 1% Symphytum officinale | | 1% Haberlea rhodopensis | | Mixture: 2% Calendula officinalis 1% Symphytum officinale 1% Haberlea rhodopensis | |
|------|--------|------------|--------|------------|--------|------------|--------|------------|
| | T-Test | Regulation | T-Test | Regulation | T-Test | Regulation | T-Test | Regulation |
| PPARD | 0.03 | 7.5 | 0.01 | 3.5 | 0.00 | 19.3 | 0.2 | 4.9 | by acting as a leukocyte adhesion molecule thereby helping the affected area fight infection and/or inflammation caused by mechanical/frictional damage such as by scratching. See, PPARD remained upregulated in the presence of the mixture, evidencing an acceleration in wound healing of a structurally impaired (wounded) skin barrier. PPARD has been found to inhibit keratinocyte apoptosis and promote the re-epithelialization of the skin by enhancing keratinocyte adhesion and migration. See, e.g., Blunder et al., *Int. J. Mol. Sci.* 22(14):7354 (2021).)

The synergistic influence exhibited by the mixture of the present disclosure on certain genes associated with cell death (apoptosis), as compared to each individual ingredient, is shown in Table 6, below.

TABLE 6

| Gene | 2% *Calendula officinalis* | | 1% *Symphytum officinale* | | 1% *Haberlea rhodopensis* | | Mixture: 2% *Calendula officinalis* 1% *Symphytum officinale* 1% *Haberlea rhodopensis* | |
|---|---|---|---|---|---|---|---|---|
| | T-Test | Regulation | T-Test | Regulation | T-Test | Regulation | T-Test | Regulation |
| CSF2 | 0.0 | 5.5 | — | — | — | — | 0.36 | 48.2 |
| KITLG | 0.37 | −1.4 | 0.06 | 2.3 | 0.36 | 5.3 | 0.36 | 45.6 |

CSF2 (Colony-stimulating factor 2) was significantly upregulated in the presence of the mixture to produce an endogenous damage signal that promotes the therapeutic effects of mesenchymal stem cells by enhancing their multi-lineage differentiation and migratory capacities. CSF2 also stimulates the proliferation and differentiation of granulocytes and macrophages for addressing infection. As a result, its stimulation is believed to enhance the skin barrier's response to atopic dermatitis flareups. See, e.g., Park et al., *Mol Therapy* 27(6):1087-1100 (2019).

The synergistic influence exhibited by the mixture of the present disclosure on certain genes associated with tissue remodeling/wound healing, as compared to each individual ingredient, is shown in Table 7, below.

KITLG (stem cell factor (SCF) or mast cell growth factor) encodes the ligand for the KIT receptor tyrosine kinase. It plays a role in epidermal homeostasis and melanocyte development. It regulates skin pigmentation by controlling the proliferation, migration, and survival of melanocytes and influences melanin distribution. In atopic dermatitis, inflammatory cytokines and vasoactive intestinal peptide can cause epidermal keratinocytes to produce stem cell factor.

disease lesions like AD and psoriasis which activates the RHO family of GTPases, important regulators for diverse cellular processes, including cellular polarization and morphogenesis as well as rearrangement of the actin skeleton in cells to facilitate their removal by phagocytosis. This upregulation enables the clearance of dying keratinocytes for wound healing. See, e.g., Coleman and Olson, *Cell Death Differ.* 9:493-504 (2002) and Bang et al., *Sci Report* 12:5889 (2022).

GRHL3-transcription factor, which activates gene expression programs required for cell adhesion, lipid production, cornified envelope formation and protein crosslinking, was significantly upregulated by the mixture (almost three times more than in *Calendula* alone showing amplificatory synergy). It is essential for skin barrier formation and adult epidermal repair. This upregulation helps to reinforce and restore the stratum corneum. See, e.g., Klein et al., *PLOS Genet.* e1006745 (2017).

PAX3 was upregulated by the mixture. The protein made by the PAX3 gene directs the activity of other genes that signal neural crest cells to form specialized tissues or cell types including nerve cells and melanocytes. Upregulation of this gene therefore serves to support melanocyte differentiation, survival, proliferation, and migration for healing inflamed regions of skin and local hair follicles. See, e.g., Boudjadi et al., *Gene* 666:145-157 (2018) and Medic et al., *Biochem. Biophys. Res. Comm.* 411(4):832-837 (2011).

TABLE 7

| Gene | 2% *Calendula officinalis* | | 1% *Symphytum officinale* | | 1% *Haberlea rhodopensis* | | Mixture: 2% *Calendula officinalis* 1% *Symphytum officinale* 1% *Haberlea rhodopensis* | |
|---|---|---|---|---|---|---|---|---|
| | T-Test | Regulation | T-Test | Regulation | T-Test | Regulation | T-Test | Regulation |
| BMP4 | — | — | — | — | — | — | 0.07 | 2.0 |
| GRHL3 | 0.06 | 1.7 | — | — | — | — | 0.01 | 5.2 |
| PAX3 | — | — | — | — | — | — | 0.07 | 1.8 |
| SERPINH1 | — | — | — | — | — | — | 0.01 | −1.5 |
| TIMP2 | — | — | — | — | — | — | 0 | −1.4 |

Various tissue remodeling and wound healing genes that help mitigate alterations in skin barrier structure in regions suffering from AD or psoriatic inflammation were influenced by the mixture, as compared to each individual ingredient.

BMP4 was upregulated by the mixture. This gene has been observed as an upstream regulator in skin inflammatory SERPINH1 which encodes for Hsp47 (heat shock protein), a collagen-specific molecular chaperone that localizes in the endoplasmic reticulum (ER), is indispensable for molecular maturation of collagen by ensuring correct folding of procollagen. This gene was downregulated in the presence of the mixture to decrease procollagen folding in the early stages of wound healing to allow for the fibroblasts to accumulate more components such as hyaluronan and fibronectin in the extracellular matrix and not form scar tissue within the inflammatory lesions. See, e.g., Tyavambiza et al., *Bioengineering* 9(11):712 (2022) and Ito and Nagata, *Seminar Cell Dev. Biol.* 62:142-151 (2017).

TTIW2 inhibits several MMPs that cleave a range of substrates that impact structural and cellular aspects of tissue architecture. This gene was downregulated in the presence of the mixture, thereby enabling it to maximize the effectiveness of those MMP genes involved in tissue remodeling/wound healing. See, e.g., Costanzo et al., *Pulm. Med.* 2022:3632764 (2022).

In summary, the gene expression data of Tables 1-7 establishes the synergy realized by combining the ingredients of the present disclosure when it comes to treating and managing oxidative stress, inflammation, and skin barrier/SC restructuring and repair to help mitigate symptoms associated with inflammatory skin disorders.

Example 2

A composition in accordance with the present disclosure was prepared having the following ingredients:

| Ingredients | % wt/wt |
|---|---|
| *Haberlea rhodopensis* | 1.0 |
| *Calendula officinalis* | 2.0 |
| *Symphytum officinale* | 2.5 |
| *Padina pavonica Thallus* | 2.0 |
| Colloidal oatmeal | 1.0 |
| emulsifiers | 2.0 |
| *Lactobacillus* ferment | 3.0 |
| Coconut fermented and/or mixed with *Lactobacillus* | 2.0 |
| Potassium sorbate | 0.2 |
| 1,3-propanediol | 4.0 |
| *Ceramide* | 0.01 |
| Sodium benzoate | 0.2 |
| Hydrolyzed sodium hyaluronate | 0.1 |
| Deionized water | 64.9 |
| additives | q.s. |
| Total | 100 |

The composition of Example 2 was clinically tested on a first cohort of test subjects all of whom exhibited active signs of atopic dermatitis including skin flakiness, irritation, itch, and intense dryness, to determine its efficacy in treating and managing the symptoms associated with atopic dermatitis. Each of the test subjects had a SCORAD, a clinical tool used to score atopic dermatitis, measured by a dermatologist of between 25-50. An EASI score which is a tool used to measure the extent (area) and severity of atopic eczema was also calculated by a dermatologist for each test subject. Thirty-four individuals (10 male and 24 female), aged 22-52, were asked to apply the composition twice a day at home, once in the morning and once in the evening, under normal use conditions, as a replacement for their normal skin treatment routine. Skin health and appearance data was collected on both the treated and non-treated areas of each test subject.

SCORAD data involving measurement of atopic exacerbations was obtained by a dermatologist on day 0 (DO) and day 56 (D56). Scoring parameters included the extent, intensity, and subjective evaluation of atopic exacerbations experienced by each test subject. The data showed that 100% of the subjects tested experienced a significant decrease of, on average, 94% in their SCORAD score on D56, a completely unexpected and surprising discovery.

In addition, 97% of subjects tested experienced a significant decrease of 93%, on average, in the extent of atopic exacerbations, 100% of subjects tested experienced, on average, a 94% decrease in the intensity of atopic exacerbations, and 94% of subjects tested experienced, on average, a 96% decrease in the severity of their symptoms based on their subjective evaluation. Moreover, 100% of subjects tested experienced, on average, an 89% decrease in the number of atopic exacerbations present on their body at D56.

The efficacy of the composition of Example 2 was also assessed using the Eczema Area Severity Index (EASI) scoring system for both the treated versus non-treated area. An EASI score is calculated by a dermatologist who assigns a value of from 0-72 (1.1 to 7 indicates mild disease and 7.1 to 21 indicates moderate disease), for each of the following symptoms: erythema, infiltration/papulation, excoriation, and lichenification. The EASI score corresponds to the sum of these values wherein the lower the score, the more efficacious the composition.

Regarding the untreated zone, only 6% of test subjects experienced a statistically insignificant decrease (improvement) in their EASI score at day 28 (D28) and D56.

Conversely, 85% of the test subjects experienced a 52% decrease of their EASI score at D28, and 100% experienced a 95% decrease in their EASI score at D56.

Next, the composition of Example 2 was evaluated to determine its effect on skin moisturization/hydration. Moisturization/hydration data was obtained using a corneometer, wherein an increase in corneometer value corresponds to an increase in moisturization/hydration. Regarding the untreated zone without active lesion, 3% of test subjects experienced a statistically insignificant 1% decrease in cutaneous hydration at D28, and 9% experienced a statistically insignificant 1% decrease at D56.

Conversely, for the treated zone, the data showed that 97% of test subjects experienced a statistically significant increase in cutaneous hydration of more than 42% on day 28; and 100% of test subjects experienced an increase of more than 78% on day 56.

The efficacy of the composition was also evaluated to determine its effect on transepidermal water loss (TEWL), which is indicative of skin barrier health and functionality. The measurements were performed using a Tewameter™ 300® on both the treated and untreated zones on DO, D28, and D56. Regarding the untreated zone without active lesion, 6% of test subjects experienced a statistically insignificant 0% decrease in TEWL at D28; and 9% experienced a statistically insignificant 1% increase in TEWL at D56.

Conversely, for the treated zone, the data showed that 88% of the test subjects experienced a statistically significant 22% decrease in TEWL at D28; and 100% of test subjects experienced a statistically significant 40% decrease in TEWL at D56.

Next, the composition of Example 2 was clinically evaluated to determine its effect on eczematous lesions by measuring its exfoliating effect using a Skin Image Analyser (S.I.A.®) in combination with QuantiSquam® software. The studied parameters included the desquamation index and surface occupied by squamae (in mm2). A decrease in one of these parameters is characteristic of an exfoliating effect.

Regarding the surface occupied by squamae for the non-treated zone, 55% of test subjects experienced a 44% decrease in squamae area at D56.

Conversely, for the treated zone, the data showed that 88% of test subjects experienced a 49% decrease in squamae area at D28, and 87% of those tested experienced a 64% decrease at D56.

The efficacy of the composition was also evaluated with respect to desquamation index which represents the ratio between occupied surface and the thickness of their cellular layers.

For the untreated area, 84% of subjects experienced an average decrease of 45% at D56.

Conversely, 91% of subjects experienced a 51% decrease on D28, and 87% of subjects experienced a decrease of 65% at D56.

A questionnaire, created by the clinical trial center, was given to each test subject for them to subjectively evaluate the soothing efficacy of the composition with respect to the itching and burning sensation they were experiencing.

With respect to itching sensation, 88% of test subjects experienced a 71% decrease in itching sensation at D28, and 91% experienced a decrease of 93% at D56.

Regarding burning sensation, 44% of test subjects experienced an average decrease of 69% in burning sensation at D28, and 53% experienced a decrease of 79% at D56.

Example 3

The composition of Example 2 was clinically tested on a second cohort of test subjects suffering from atopic dermatitis. In this Example, topical application of the composition was tested in combination with administration of a dietary supplement containing the following ingredients:

| Ingredient | Weight |
| --- | --- |
| L-Histidine | 4 grams |
| Aristotelia chilensis leaf extract | 2 g |
| Ugni molinae leaf extract | 2 g |
| Buddleja globosa leaf extract | 2 g |

Each of the test subjects had an initial SCORAD value measured by a dermatologist of between 25-50. An EASI score was also calculated by a dermatologist for each test subject. Thirty-three individuals aged 19-73, were asked to orally consume the dietary supplement once a day, and to apply the composition onto the surface of their skin twice a day at home, once in the morning and once in the evening, under normal use conditions, as a replacement for their normal skin treatment routine. The subjects were also asked to cleanse their skin with an unscented/neutral soap cleanser prior to applying the composition. Skin health and appearance data was collected on both the treated area (composition plus supplement) and non-treated area (supplement only) for each test subject.

SCORAD data involving measurement of atopic exacerbations was obtained by a dermatologist on D0 and D56. Scoring parameters included the extent, intensity, and subjective evaluation of atopic exacerbations experienced by each test subject.

The data corresponding to the treated area showed that 100% of the subjects tested experienced a significant decrease of, on average, 93% in their SCORAD at D56.

In addition, 100% of subjects experienced an average decrease of 94% for extent of atopic exacerbations, 100% of subjects tested experienced an average decrease of 92% for intensity of atopic exacerbations, and 97% of subjects tested experienced an average decrease of 94% in severity of their symptoms based on their subjective evaluation, all at D56. Moreover, 97% of subjects tested experienced, on average, a 92% decrease in the number of atopic exacerbations present on their body at D56.

The efficacy of the combination of the composition of Example 2 and the dietary supplement was also assessed using the Eczema Area Severity Index (EASI) scoring system for both the treated versus non-treated area. An EASI score is calculated by a dermatologist who assigns a value of from 0-72 (with 1.1 to 7 representing mild disease and 7.1 to 21 representing moderate disease), for each of the following symptoms: erythema, infiltration/papulation, excoriation, and lichenification. The EASI score corresponds to the sum of these values wherein the lower the score, the more efficacious the composition.

Regarding the untreated (supplement only) zone, 9% of test subjects experienced a statistically significant 29% decrease (improvement) in their EASI score at 28, and 12% of test subjects experienced a statistically significant 67% decrease (improvement) in their EASI score at D56.

Regarding the treated (composition+supplement) area, 91% of the test subjects experienced a 62% decrease of their EASI score at 28, and 100% of the test subjects experienced a 90% decrease of their EASI score at D56, as compared to D0.

Next, the combination of the composition of Example 2 and the dietary supplement was evaluated to determine its effect on skin moisturization/hydration. Moisturization/hydration data was obtained using a corneometer, wherein an increase in corneometer value corresponds to an increase in moisturization/hydration (i.e., cutaneous hydration).

Regarding the untreated (supplement only) zone, 73% of test subjects experienced a statistically significant 14% increase in cutaneous hydration at D56.

For the treated (composition+supplement) zone, the data showed that 94% of test subjects experienced a statistically significant average increase in cutaneous hydration of 85% at D28, and 91% experienced a statistically significant average increase in cutaneous hydration of 117% at D56.

The efficacy of the combination of the composition of Example 2 and the dietary supplement was also evaluated to determine its effect on transepidermal water loss (TEWL), which is indicative of skin barrier health and functionality. The measurements were performed using a Tewameter™ 300® on both the treated and untreated zones on D0 and D56.

Regarding the untreated (supplement alone) zone, no statistically significant decrease in TEWL was observed.

For the treated (composition+supplement) zone, the data showed that 77% of the test subjects experienced a statistically significant average decrease of 25% in TEWL at D28, and 79% of the test subjects experienced a statistically significant average decrease of 29% in TEWL at D56.

Next, the combination of the composition of Example 2 and the dietary supplement was clinically evaluated to determine its effect on eczematous lesions by measuring its exfoliating effect using a Skin Image Analyser (S.I.A.®) in combination with QuantiSquam® software. The studied parameters included the desquamation index and surface occupied by squamae (in mm2). A decrease in one of these parameters is characteristic of an exfoliating effect.

Regarding the surface area occupied by squamae for the non-treated (supplement only) zone, 72% of test subjects experienced a 56% decrease in squamae surface area at D56.

For the treated (composition+supplement) zone, the data showed that 81% of test subjects experienced a 65% decrease in squamae surface area at D28, and 97% of test subjects experienced an 82% decrease in squamae surface area at D56.

A questionnaire, created by the clinical trial center, was given to each test subject for them to subjectively evaluate the soothing efficacy of the composition plus supplement with respect to the itching and burning sensation they were experiencing.

With respect to itching sensation, 88% of test subjects experienced a 72% decrease in itching sensation at D28, and 97% of test subjects experienced an 88% decrease in itching sensation at D56.

Regarding burning sensation, 30% of test subjects experienced a 56% decrease in burning sensation at D28, and 45% of test subjects experienced an 84% decrease in burning sensation at D56.

Based on the above data, it is undeniably both surprising and unexpected that the compositions of the present invention, both alone and in combination with the dietary supplement, are compellingly efficacious in not only repairing/reinforcing the skin barrier (SC), but also in reducing inflammation, itchiness, and eczematous lesions. The above-referenced examples establish the effectiveness of the disclosed embodiments to treat and manage symptoms associated with inflammatory skin disorders such as dermatitis and, by extension, any other type of chronic inflammatory disorder such as psoriasis. Specifically, the synergistic influence exerted on certain genes associated with (i) skin barrier repair/restructuring, (ii) inflammation reduction/management, and (iii) reduction/management of oxidative stress caused by ROS in the presence, coupled with the completely astonishing clinical data for the compositions on their own and in combination with the dietary supplement, evidence the compelling efficacy of the present invention when it comes to the treatment and management of symptoms associated with such inflammatory skin disorders. Moreover, consistent use of the disclosed embodiments can help reduce reliance on corticosteroids for symptom relief.

What is claimed is:

1. A composition for application onto human skin comprising: (1) a synergistic blend of at least: (a) from about 0.1 to about 5.0% by weight of *Calendula officinalis* extract; (b) from about 0.1 to about 5.0% by weight of *Symphytum officinale* extract; (c) from about 0.1 to about 5.0% by weight of a biotech-derived *Haberlea rhodopensis* extract; and (d) from about 0.1 to about 5% by weight of *Padina pavonica thallus* extract; and (2) a skin protectant active ingredient, all weights based on total weight of the composition, wherein the composition is capable of increasing ceramide production and reducing permeability of the skin barrier.

2. The composition of claim 1, wherein (2) is present in an amount of from about 0.01 to about 500 by weight, all weights based on total weight of the composition.

3. The composition of claim 1, wherein (a) is present in an amount of from about 0.5 to about 4% by weight; (b) is present in an amount of from about 0.1 to about 4% by weight; (c) is present in an amount of from about 0.5 to about 4% by weight; and (d) is present in an amount of from about 0.5 to about 4% by weight; and (2) is present in an amount of from about 0.02 to about 3% by weight, all weights based on total weight of the composition.

4. The composition of claim 1, wherein (a) is present in an amount of from about 1 to about 3% by weight; (b) is present in an amount of from about 0.4 to about 3% by weight; (c) is present in an amount of from about 0.75 to about 2% by weight; (d) is present in an amount of from about 1 to about 3% by weight; and (2) is present in an amount of from about 0.5 to about 2% by weight, all weights based on total weight of the composition.

5. The composition of claim 1, wherein skin protectant active ingredient is colloidal oatmeal.

6. The composition of claim 1, further comprising at least one humectant.

7. The composition of claim 6, wherein the at least one humectant is present in an amount of from about 0.1 to about 10% by weight, based on total weight of the composition.

8. The composition of claim 6, wherein the at least one humectant comprises hyaluronic acid.

9. The composition of claim 1, further comprising at least one ceramide.

10. The composition of claim 9, wherein the at least one ceramide is present in an amount of from about 0.01 to about 0.5% by weight, based on total weight of the composition.

11. The composition of claim 9, wherein the at least one ceramide is selected from ceramide 1, ceramide 2, ceramide 3, ceramide 4, ceramide 5, ceramide 1A, ceramide 6 II, ceramide AP, ceramide EOP, ceramide EOS, ceramide NP, ceramide NG, ceramide NS, ceramide AS, and ceramide NS dilaurate.

12. A composition for application onto human skin comprising: (1) a synergistic blend of at least: (a) from about 0.1 to about 5.0% by weight of *Calendula officinalis* stem cell extract; (b) from about 0.1 to about 5.0% by weight of *Symphytum officinale* extract; (c) from about 0.1 to about 5.0% by weight of a biotech-derived *Haberlea rhodopensis* extract; and (d) from about 0.1 to about 5% by weight of *Padina pavonica thallus* extract; (2) at least one skin protectant active ingredient; (3) at least one humectant; and (4) at least one ceramide, all weights based on total weight of the composition, wherein the composition is capable of increasing ceramide production and reducing permeability of the skin barrier.

13. The composition of claim 12, wherein (2) is present in an amount of from about 0.01 to about 5% by weight, all weights based on total weight of the composition.

14. The composition of claim 12, wherein (a) is present in an amount of from about 0.5 to about 4% by weight; (b) is present in an amount of from about 0.1 to about 4% by weight; (c) is present in an amount of from about 0.5 to about 4% by weight; and (d) is present in an amount of from about 0.5 to about 4% by weight; and (2) is present in an amount of from about 0.02 to about 3% by weight, all weights based on total weight of the composition.

15. The composition of claim 12, wherein (a) is present in an amount of from about 1 to about 3% by weight; (b) is present in an amount of from about 0.4 to about 3% by weight; (c) is present in an amount of from about 0.75 to about 2% by weight; (d) is present in an amount of from about 1 to about 3% by weight; and (2) is present in an amount of from about 0.5 to about 2% by weight, all weights based on total weight of the composition.

16. A method of ameliorating and managing symptoms associated with chronic inflammatory skin disorders comprising applying a composition containing: (1) a synergistic blend of at least: (a) from about 0.1 to about 5.0% by weight of *Calendula officinalis* extract; (b) from about 0.1 to about 5.0% by weight of *Symphytum officinale* extract; (c) from about 0.1 to about 5.0% by weight of a biotech-derived *Haberlea rhodopensis* extract; and (d) from about 0.1 to about 5% by weight of *Padina pavonica thallus* extract; and (2) at least one skin protectant active ingredient, onto skin, wherein all weights based on total weight of the composition, and wherein the composition is capable of increasing ceramide production and reducing permeability of the skin barrier.

17. The method of claim 16, wherein (2) is present in an amount of from about 0.01 to about 5% by weight, all weights based on total weight of the composition.

18. The method of claim 16, wherein (a) is present in an amount of from about 0.5 to about 4% by weight; (b) is present in an amount of from about 0.1 to about 4% by weight; (c) is present in an amount of from about 0.5 to about 4% by weight; and (d) is present in an amount of from about 0.5 to about 4% by weight; and (2) is present in an amount of from about 0.02 to about 3% by weight, all weights based on total weight of the composition.

19. The method of claim 16, wherein (a) is present in an amount of from about 1 to about 3% by weight; (b) is present in an amount of from about 0.4 to about 3% by weight; (c) is present in an amount of from about 0.75 to about 2% by weight; (d) is present in an amount of from about 1 to about 3% by weight; and (2) is present in an amount of from about 0.5 to about 2% by weight, all weights based on total weight of the composition.

20. The method of claim 16, further comprising orally administering a dietary supplement containing: (i) *Buddleja globosa* leaf extract, (ii) *Aristotelia chilensis* leaf extract, (iii) *Ungi molinae* leaf extract, and (iv) L-histidine.

21. The method of claim 20, wherein (i) is present in an amount of from about 0.5 to about 3 mg; (ii) is present in an amount of from about 1 to about 10 mg; (iii) is present in an amount of from about 0.5 to about 3 mg; and (iv) is present in an amount of from about 0.1 to about 5 mg, all weights based on the total dry weight of the dietary supplement.

22. The method of claim 20 wherein (i) is present in an amount of from about 1 to about 2 mg; (ii) is present in an amount of from about 2 to about 5 mg; (ii) is present in an amount of from about 1 to about 2 mg; and (iv) is present in an amount of from about 0.2 to about 4 mg, all weights based on the total dry weight of the dietary supplement.

23. The method of claim 20, wherein the supplement is administered daily.

24. The method of claim 16, further comprising: cleansing the skin with a microbiome-friendly soap prior to application of the composition, and/or applying a topical composition containing a bacteriophage capable of killing *S. aureus* bacterium.

25. The method of claim 20, further comprising: cleansing the skin with a microbiome-friendly soap prior to application of the composition, and/or applying a topical composition containing a bacteriophage capable of killing *S. aureus* bacterium.

26. The method of claim 16 wherein the chronic inflammatory skin disorder is dermatitis, psoriasis, or a combination thereof.

27. He method of claim 20 wherein the chronic inflammatory skin disorder is dermatitis, psoriasis, or a combination thereof.

28. The method of claim 16, further comprising orally administering a probiotic supplement comprising a therapeutically effective amount of: (A) a probiotic blend of bacterial components comprising at least: (i) *Lactobacillus helveticus*, (ii) *Lactobacillus plantarum*, (iii) *Bifidobacterium longum*, and (iv) *Streptococcus thermophilus*; and (B) at least one plant-based, antioxidant-rich source of fiber.

29. The method of claim 16, further comprising topically applying a probiotic serum comprising live *Lactobacillus plantarum* lactobacilli onto the skin.

* * * * *